United States Patent [19]  [11] 4,045,560
Sunagawa et al.  [45] Aug. 30, 1977

[54] 2-MORPHOLINE CONTAINING METHANO OR ETHANO ANTHRACENE COMPOUNDS

[75] Inventors: Makoto Sunagawa; Hiromi Sato; Junki Katsube, all of Osaka; Hisao Yamamoto, Kobe, all of Japan

[73] Assignee: Sumitomo Chemical Company, Limited, Japan

[21] Appl. No.: 703,128

[22] Filed: July 7, 1976

[30] Foreign Application Priority Data

July 7, 1975 Japan ............................. 50-83870

[51] Int. Cl.$^2$ .................. C07D 265/30; A61K 31/535
[52] U.S. Cl. ............................ 424/248.4; 424/248.5; 424/248.53; 260/348.11; 260/488 CD; 260/497 R; 260/515 A; 260/515 D; 260/558 R; 260/668 F; 544/154
[58] Field of Search ........ 260/247, 247.1 E, 247.2 R; 424/248.4, 248.5, 248.53

[56] References Cited

U.S. PATENT DOCUMENTS

| 3,399,201 | 8/1968 | Schmidt et al. | 240/247 |
|---|---|---|---|
| 3,489,799 | 1/1970 | Schmidt et al. | 260/247 |
| 3,778,467 | 12/1973 | Wilhelm et al. | 260/239 R |
| 3,821,214 | 6/1974 | Wilhelm et al. | 260/247 |

OTHER PUBLICATIONS

"Tetrahedron", vol. 25 (1969), p. 3428s.
"J. Org. Chem.", vol. 26 (1961), p. 4281.

*Primary Examiner*—Alan L. Rotman
*Assistant Examiner*—R. W. Ramsuer
*Attorney, Agent, or Firm*—Birch, Stewart, Kolasch and Birch

[57] ABSTRACT

Novel morpholine compounds of the formula:

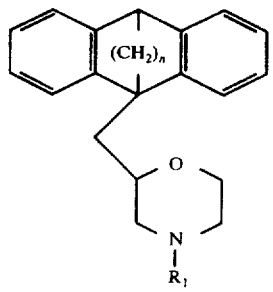

wherein $R_1$ represents hydrogen, $C_1$–$C_4$ alkyl, $C_3$–$C_5$ alkenyl, aryl($C_1$–$C_4$)alkyl or ($C_3$–$C_6$)cycloalkyl($C_1$–$C_4$)alkyl and n represents 1 or 2, and their non-toxic salts, which are useful as antidepressants and can be produced by various methods.

7 Claims, No Drawings

2-MORPHOLINE CONTAINING METHANO OR ETHANO ANTHRACENE COMPOUNDS

The present invention relates to novel morpholine derivatives and their production and use.

The novel morpholine derivatives provided by this invention are morpholine compounds of the formula:

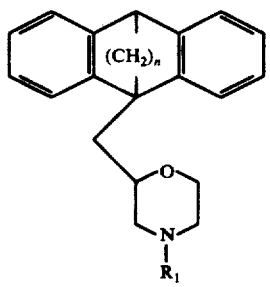

[I]

wherein $R_1$ is hydrogen, $C_1$-$C_4$ alkyl, $C_3$-$C_5$ alkenyl, aryl($C_1$-$C_4$)alkyl or ($C_3$-$C_6$)cycloalkyl($C_1$-$C_4$)alkyl and $n$ is 1 or 2, and their non-toxic salts.

In the above significances, as "$C_1$-$C_4$ alkyl," there may be exemplified methyl, ethyl, n-propyl, isopropyl, n-butyl, etc. The term "$C_3$-$C_5$ alkenyl" may include allyl, 3,3-dimethylallyl, etc. Examples of "aryl($C_1$-$C_4$) alkyl" are benzyl, phenethyl, etc. Examples of "($C_3$-$C_6$) cycloalkyl($C_1$-$C_4$)alkyl" are cyclopropylmethyl, cyclopropylethyl, etc.

The morpholine compounds [I] may form acid addition salts (e.g. hydrochloride, hydrobromide, sulfate, acetate, oxalate, citrate, succinate, fumarate, lactate) and quaternary ammonium salts (e.g. methochloride, methiodide).

The morpholine compounds [I] and their non-toxic salts exhibit pharmacological activities and are useful as medicines. In general, they affect the functioning of the central nervous system. That is, they antagonize the central nervous system depressant effect induced by tetrabenazine and by reserpine, and also potentiate the central action of norepinephrine. Therefore, they are useful as antidepressants.

Among the morpholine compounds [I] of the invention, the morpholine compounds [I] wherein $n$ is 1 and their non-toxic salts are preferable. The morpholine compounds [I] wherein $R_1$ is hydrogen, methyl or benzyl and $n$ is 1 and their non-toxic salts are particularly preferable.

The morpholine compounds [I] and their non-toxic salts can be administered parenterally or orally with dosage adjusted to individual requirements (10 - 300 mg/human body (60 kg of body weight)/day) in the form of conventional pharmaceutical preparations which may include a pharmaceutically acceptable carrier or diluent. For instance, they may be administered in the form of a conventional solid pharmaceutical preparation such as tablets or capsules or in the form of a conventional liquid pharmaceutical preparation such as suspensions, emulsions or solutions.

The morpholine compounds [I] may be prepared by various methods, among which typical examples are as follows:

a. The morpholine compound [I] can be prepared by reduction of the lactam of the formula:

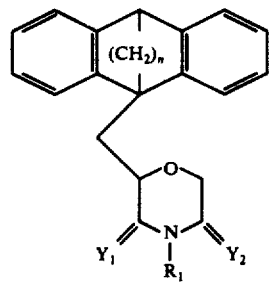

[II]

wherein $R_1$ and $n$ are each as defined above, $Y_1$ represents an oxygen atom or two hydrogen atoms and $Y_2$ represents an oxygen atom when $Y_1$ is two hydrogens or $Y_2$ represents two hydrogen atoms when $Y_1$ is oxygen.

The reduction may be accomplished by the use of a reducing agent as conventionally employed for reduction of a lactam

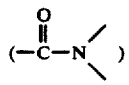

to an amine

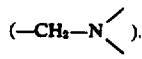

One of the preferred reducing agents is a metal hydride such as lithium aluminum hydride, sodium bis(2-methoxyethoxy)aluminum hydride, sodium dihydrodiethyl aluminate or sodium borohydride. The reducing agent can be used in an equimolar amount or more with respect to the compound [II]. In case of using sodium borohydride as the reducing agent, the presence of a salt such as aluminum chloride is favored. When desired, an inert solvent such as an ether (e.g. diethyl ether, tetrahydrofuran, dioxane, ethyleneglycol dimethyl ether), an aliphatic hydrocarbon (e.g. heptane, n-hexane, cyclohexane), an aromatic hydrocarbon (e.g. benzene, toluene) or their mixture may be employed in the reduction. The temperature for the reduction can be varied widely from ice-cooling to the refluxing temperature of the reduction system.

b. The morpholine compound [I] can be prepared by reacting the epoxide of the formula:

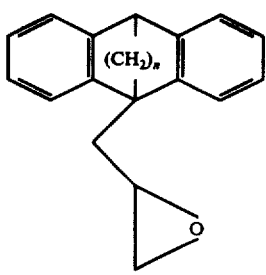

[III]

wherein $n$ is as defined above with the amine of the formula:

[IV]

wherein $R_1$ is as defined above and X is a conventional leaving group such as halogen (e.g. chlorine, bromine) or sulfonyloxy (e.g. $-OSO_2R_9$ wherein $R_9$ is hydroxyl, $C_1-C_3$ alkyl, polyhalo($C_1-C_3$)alkyl, aryl, $C_1-C_3$ alkoxy or aryloxy), followed by treatment with a base.

The reaction of the epoxide [III] with the amine [IV] is usually carried out in an inert solvent such as an alcohol (e.g. methanol, ethanol, isopropanol, ethylene glycol), an ether (e.g. diethyl ether, tetrahydrofuran, dioxane), an aromatic hydrocarbon (e.g. benzene, toluene) or their mixture in the presence of a base such as a metal hydroxide (e.g. sodium hydroxide, potassium hydroxide, barium hydroxide) at a wide range of temperature from room temperature to the refluxing temperature of the reaction system.

As the reaction product, there is obtained the aminoalcohol of the formula:

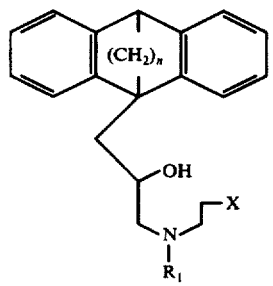

[V]

wherein $R_1$, $n$ and X are each as defined above, which is then subjected to treatment with a base with or without the previous separation from the reaction mixture. The treatment may be carried out at a temperature from ice-cooling to the refluxing temperature of the reaction system. As the base, there may be employed a metal hydroxide (e.g. sodium hydroxide, potassium hydroxide, barium hydroxide), usually in an equimolar amount or more. The use of an inert solvent such as methanol, ethanol, tetrahydrofuran, dioxane, benzene or toluene is normally preferred.

c. The morpholine compound of the formula:

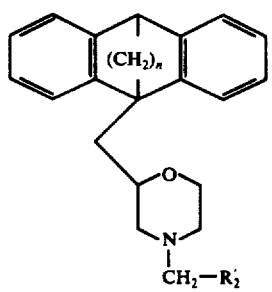

[Ia]

wherein $R_2'$ is hydrogen, $C_1-C_3$ alkyl, $C_2-C_4$ alkenyl, aryl, ($C_3-C_6$)cycloalkyl, ($C_3-C_6$)cycloalkyl($C_1-C_3$)alkyl or aryl($C_1-C_3$)alkyl and $n$ is as defined above can be prepared by reducing the morpholine compound of the formula:

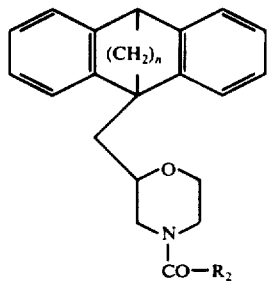

[VI]

wherein $R_2$ is hydrogen, $C_1-C_3$ alkyl, $C_2-C_4$ alkenyl, aryl, ($C_3-C_6$)cycloalkyl, ($C_3-C_6$)cycloalkyl($C_1-C_3$)alkyl, aryl($C_1-C_3$)alkyl or $C_1-C_4$alkoxy and $n$ is as defined above.

The reduction may be carried out in the substantially same manner as in Method (a).

d. The morpholine compound of the formula:

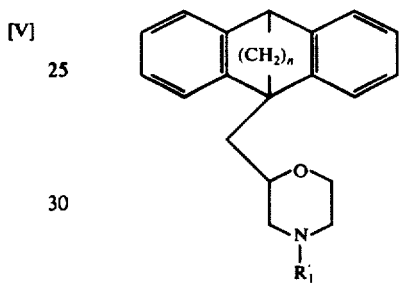

[Ib]

wherein $R_1'$ is $C_1-C_4$ alkyl, $C_3-C_5$ alkenyl, aryl($C_1-C_4$)alkyl or ($C_3-C_6$)cycloalkyl($C_1-C_4$)alkyl and $n$ is as defined above can be prepared by condensation of the morpholine compound of the formula:

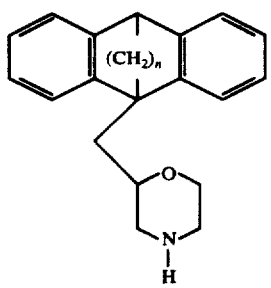

[Ic]

wherein $n$ is as defined above with a compound of the formula:

$Z-R_1'$ [VII]

wherein Z is a conventional leaving group such as halogen (e.g. chlorine, bromine, iodine) or sulfonyloxy (e.g. methanesulfonyloxy, p-toluenesulfonyloxy, trichloromethylsulfonyloxy) and $R_1'$ is as defined above.

The condensation may be effected in an inert solvent such as an aromatic hydrocarbon (e.g. benzene, toluene, xylene), dimethylformamide, dimethylsulfoxide, an alcohol (e.g. methanol, ethanol, propanol) or their mixture in the presence of a base. Examples of the base are a metal carbonate (e.g. sodium carbonate, potassium carbonate), a metal hydroxide (e.g. sodium hydroxide, potassium hydroxide), a metal hydride (e.g. sodium hydride, potassium hydride), a metal amide (e.g. sodium amide, potassium amide), an alkylamine (e.g. triethylamine, pyridine) or a metal alkoxide (e.g. sodium methoxide, sodium ethoxide, potassium t-butoxide). The base may be used in a stoichiometric amount or more. The temperature for the condensation can be varied from room temperature to the refluxing temperature.

e. The morpholine compound [Ia] can be prepared by condensation-reduction of the corresponding morpholine compound [Ic] with a carbonyl compound of the formula:

R₂'—CHO   [VIII]

wherein R₂' is as defined above.

The condensation-reduction may be accomplished by per se known procedures. The usual procedure of the Leuckart-Wallach reaction using formic acid is applicable to the condensation-reduction [Organic Reactions, Vol. 5, p. 301, John Wiley & Sons, Inc.]. For instance, the compound [VIII] is added to a mixture of the compound [Ic] and formic acid or the amine formate as formed between them, and the resultant mixture is heated at a temperature from room temperature to about 200° C.

The condensation-reduction can be also accomplished by hydrogenation of a mixture of the compound [Ic] and the compound [VIII] over a catalyst such as Raney nickel, platinum oxide or palladium in the presence or absence of an inert solvent. The pressure may be 1 atmospheric pressure or higher. A condensation agent such as sodium acetate can be used.

The condensation-reduction can be further accomplished by using the sodium-alcohol or zinc-acid or alkali method. Examples of inert solvents utilizable in the reaction are alcohols (e.g. methanol, ethanol, isopropanol), liquid ammonia, acetic acid and ethers (e.g. diethyl ether, tetrahydrofuran, dioxane).

Moreover, the condensation-reduction can be accomplished by the reduction of the immonium or enamine prepared from the compound [Ic] and the compound [VIII] in a conventional procedure. The reduction may be performed in the same manner as the hydrogenation procedure described above. A reducing agent such as sodium borohydride, diborane, lithium aluminum hydride, sodium aluminum diethyl dihydride, sodium cyanoborohydride or bis(2-methoxyethoxy)-aluminum hydride can be used in the reduction in an inert solvent such as an alcohol (e.g. methanol, ethanol, isopropanol, n-butanol, t-butanol), an aromatic hydrocarbon (e.g. benzene, toluene), an ether (e.g. diethyl ether, diisopropyl ether, dioxane, tetrahydrofuran) or their mixture. The temperature for the treatment in this case can be varied from about −10° C to the refluxing temperature.

f. The morpholine compound [Ic] can be prepared by hydrolysis of the morpholine compound of the formula:

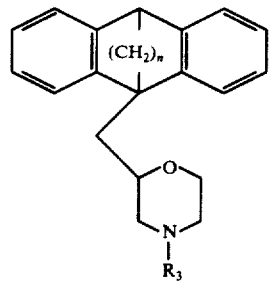

wherein R₃ is a group of the formula:

$$-\overset{O}{\underset{}{\overset{\|}{C}}}-R_2$$

in which R₂ is as defined above or nitrile and n is as defined above.

The hydrolysis may be accomplished by a conventional condition under which amide, urethane and N-cyano derivatives are hydrolyzed, for instance, by treatment with an alkali (e.g. potassium hydroxide, sodium hydroxide) or a mineral acid (e.g. hydrochloric acid, hydrobromic acid, sulfuric acid) in an inert solvent such as water, alcohols (e.g. methanol, ethanol, isopropanol, t-butanol, n-butanol, ethyleneglycol), ethers (e.g. diethyl ether, tetrahydrofuran, dioxane, ethyleneglycol dimethyl ether), aromatic hydrocarbons (e.g. benzene, toluene) or their mixture. The temperature for the treatment may be varied from ice-cooling to the refluxing temperature of the reaction system.

g. The morpholine compound [Ic] can be prepared by reductive debenzylation of the morpholine compound of the formula:

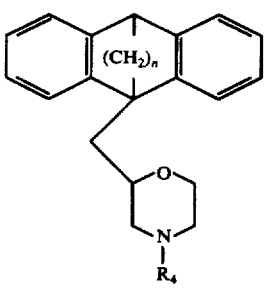

wherein R₄ is benzyl and n is as defined above.

The reductive debenzylation can be performed by a usual procedure for debenzylation of a benzyl-substituted amine. For instance, the reductive debenzylation can be accomplished by catalytic hydrogenation. The catalytic hydrogenation may be carried out in the presence of a catalyst such as platinum, palladium, ruthenium, rhodium or Raney nickel supported or not on a carrier (e.g. carbon, alumina, barium sulfate) under an atmosphere of hydrogen gas in an inert solvent such as an alcohol (e.g. methanol, ethanol, isopropanol), water, acetic acid, propionic acid, ethyl acetate or their mixture. The hydrogen pressure can be 1 atmospheric pressure or higher, and the temperature may be room temperature or higher. The presence of an acid (e.g. hydrochloric acid, hydrobromic acid, sulfuric acid, perchloric acid, acetic acid) in the reduction system may promote the progress of the reaction.

The reductive debenzylation can be also accomplished by a sodium-liquid ammonia procedure.

The morpholine compounds [I] of the invention thus produced may be separated from the reaction mixture and purified by conventional procedures.

The thus prepared morpholine compounds [I] can be converted into their salts by a conventional procedure, and reconversion from the salts to the orginal free bases can be also carried out in a conventional manner.

The starting materials for the synthesis of the morpholine compound [I], for example, may be prepared according to the following scheme A and B:

Scheme A

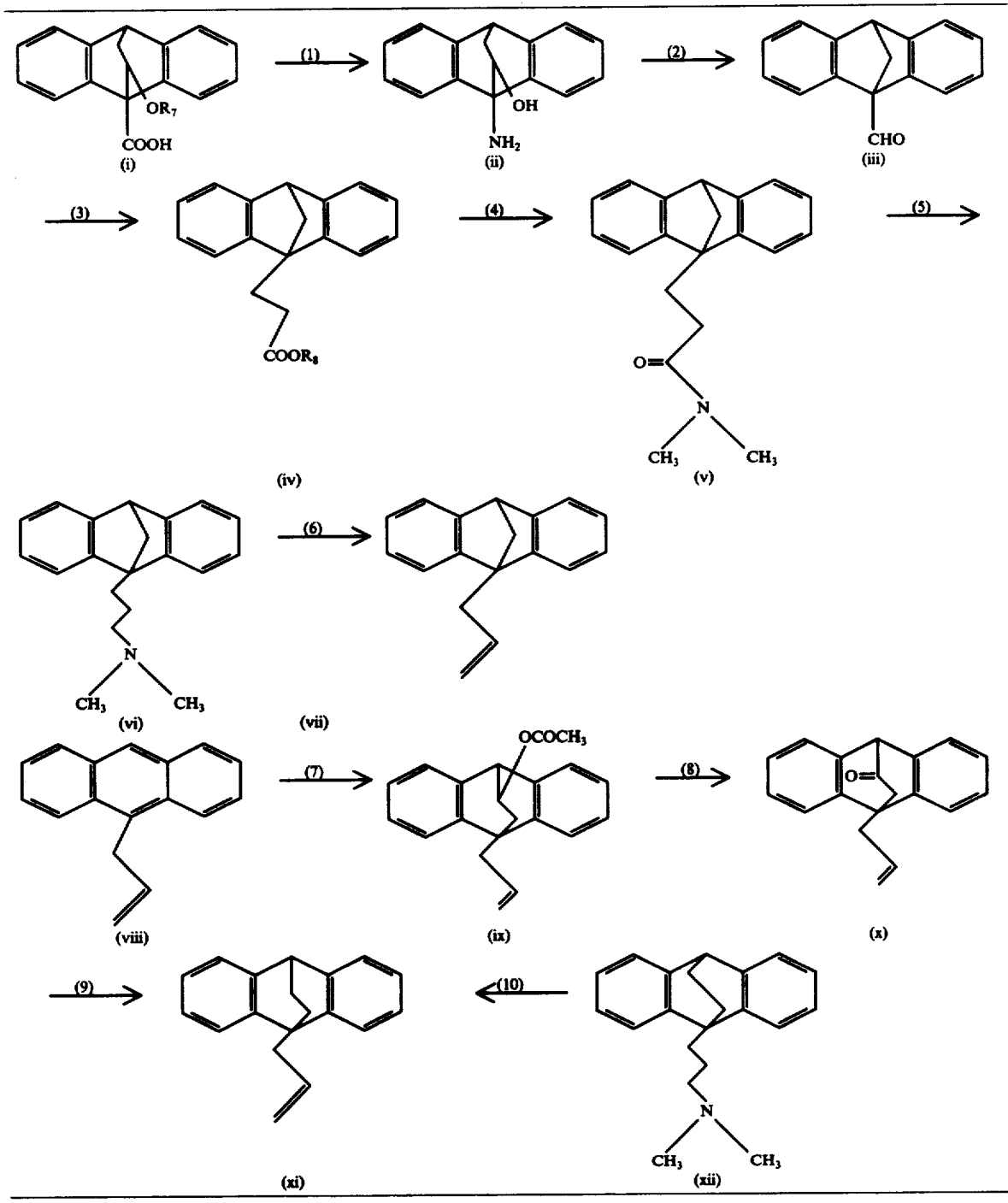

wherein $R_7$ is hydrogen or a hydroxy-protecting group such as acetyl, benzoyl or tetrahydropyranyl and $R_8$ is hydrogen or $(C_1-C_4)$alkyl. The conversion in each step may be achieved as follows:

1. 9-Amino-12-hydroxy-9,10-dihydro-9,10-ethanoanthracene (ii) can be obtained from 9-carboxy-12-hydroxy-9,10-dihydro-9,10-ethanoanthracene or its hydroxy-protecting derivative (i) through rearrangement such as the Curtius reaction or Hoffman rearrangement and hydrolysis.

2. 9-Formyl-9,10-dihydro-9,10-methanoanthracene (iii) is prepared from 9-amino-12-hydroxy-9,10-dihydro-9,10-ethanoanthracene (ii) by treatment with nitrous acid or metal nitrite in an acidic medium.

3. β-(9,10-Dihydro-9,10-methano-9-anthryl)-propionic acid or its ester derivative (iv) is prepared from 9-formyl-9,10-dihydro-9,10-methanoanthracene (iii) by a usual carbon-chain extension procedure such as the Witting reaction with triethyl phosphonoacetate, catalytic hydrogenation and hydrolysis.

4. β-(9,10-Dihydro-9,10-methano-9-anthryl)-propionic acid or its ester derivative (iv) is led to the corresponding dimethylamide derivative (v) by a usual procedure.

5. γ-Dimethylaminopropyl-9,10-dihydro-9,10-methanoanthracene (vi) is prepared from β-(9,10-dihydro-9,10-methano-9-anthryl)propionic acid dimethylamide (v) by treatment with a reducing agent such as lithium aluminum hydride or sodium bis(2-methoxyethoxy)aluminum hydride in an inert solvent.

6. 9-β-Propenyl-9,10-dihydro-9,10-methano-anthracene (vii) is obtained from 9-γ-dimethylaminopropyl-9,10-dihydro-9,10-methanoanthracene (vi) by a Hoffman elimination.

7. 9-Allylanthracene (viii) is led to 9-β-propenyl-11-acetoxy-9,10-dihydro-9,10-ethanoanthracene (ix) by a Diels-Alder reaction with vinyl acetate.

8. 9-β-Propenyl-9,10-dihydro-9,10-ethanoanthracen-11-one (x) is prepared from 9-β-propenyl-11-acetoxy-9,10-dihydro-9,10-ethanoanthracene (ix) by usual hydrolysis and oxidation.

9. 9-β-Propenyl-9,10-dihydro-9,10-ethanoanthracene (xi) is prepared from 9-β-propenyl-9,10-dihydro-9,10-ethanoanthracen-11-one (x) by a Wolff-Kishner reduction or treatment with ethanedithiol and then with hydrogen in the presence of Raney nickel.

10. 9-β-Propenyl-9,10-dihydro-9,10-ethanoanthracene (xi) is also obtainable from γ-dimethylaminopropyl-9,10-dihydro-9,10-ethanoanthracene (xii) by a Hoffman elimination.

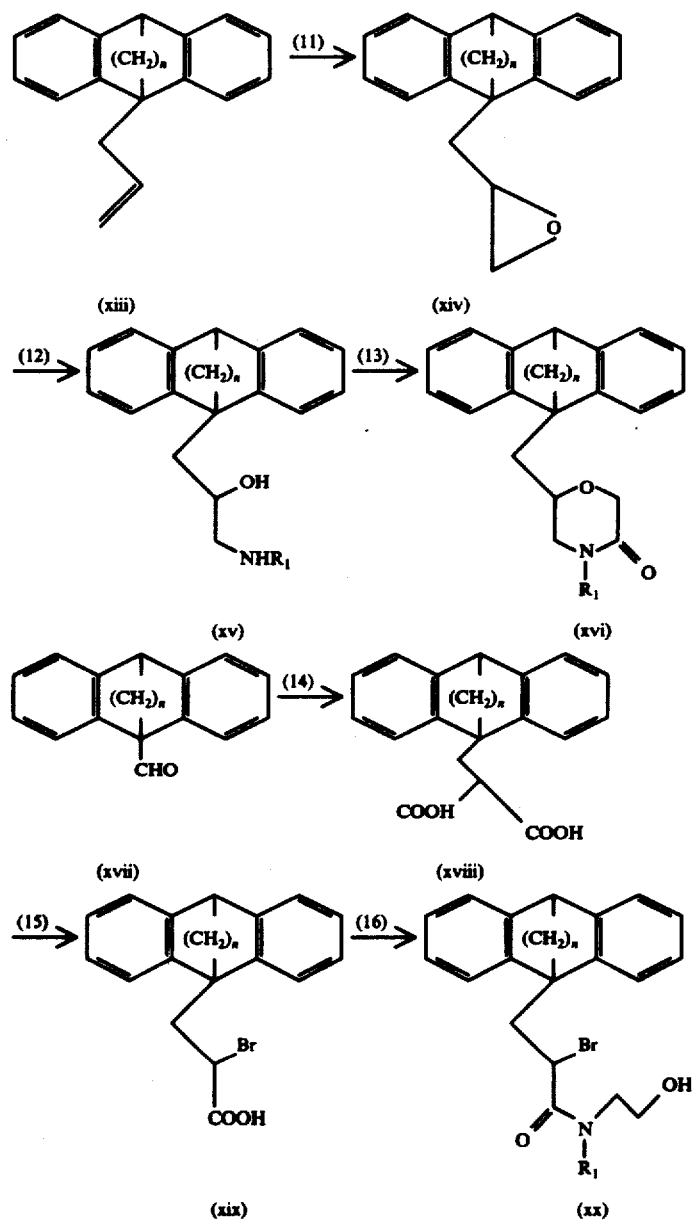

Scheme B

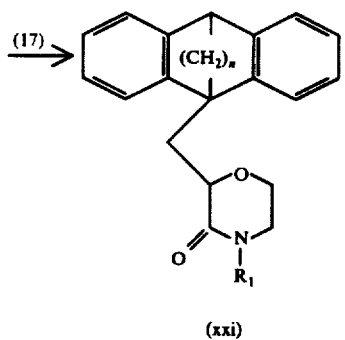

(xxi)

wherein $R_1$ and $n$ are each as defined above. The conversion in each step may be carried out as follows:

11. The epoxy compound (xiv) is prepared from the corresponding 9-β-propenyl derivative (xiii) by a usual oxidation procedure for conversion of a double bond to an epoxide.

12. The amino-alcohol compound (xv) is derived from the epoxy compound (xiv) by treatment with the corresponding amine.

13. The lactam derivative (xvi) is prepared from the amino-alcohol compound (xv) by treatment with chloroacetyl chloride or bromoacetyl bromide in the presence of a base.

14. The dicarboxylic acid compound (xviii) is prepared from the aldehyde derivative (xvii) by a Knoevenagel condensation with diethyl malonate or ethyl cyanoacetate, reduction of the double bond by catalytic hydrogenation or treatment with sodium borohydride and hydrolysis.

15. The dicarboxylic acid compound (xviii) is led to the α-bromocarboxylic acid derivative (xix) by treatment with bromine and decarboxylation.

16. The α-bromocarboxylic acid hydroxyethylamide compound (xx) is prepared by a usual amide formation procedure from the α-bromocarboxylic acid compound (xix).

17. The lactam compound (xxi) is prepared from the α-bromocarboxylic acid hydroxyethylamide compound (xx) by treatment with a base.

The morpholine compound [IX] can be prepared from the morpholine compound [Ib] by reacting with a compound of the formula:

$R_3$—Y or $R_2CO$—O—$COR_2$ wherein $R_2$ and $R_3$ are each as defined above and Y is halogen (e.g. chlorine, bromine) in a conventional acylation procedure.

The morpholine compound [IX] wherein $R_3$ is carbo($C_1$–$C_4$)alkoxy or nitrile can be also prepared from the morpholine compound of the formula:

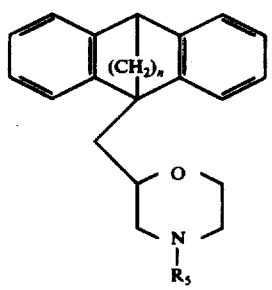

(Ie)

wherein $R_5$ is benzyl or methyl and $n$ is as defined above by treatment with a compound of the formula:

Y—$COOR_6$ or

Y—C≡N wherein $R_6$ is $C_1$–$C_4$ alkyl and Y is as defined above according to the von Braun reaction procedure.

The following examples are given to illustrate the present invention more precisely, but the present invention is not limited thereto.

EXAMPLE 1

A mixture of 9-(4-methyl-3-oxo-2-morpholinylmethyl)-9,10-dihydro-9,10-methanoanthracene (170 ml) and lithium aluminum hydride (100 mg) in dioxane was stirred at 60° - 70° C for 6 hours. Excess lithium aluminum hydride was decomposed by addition of water. The reaction mixture was diluted with ethyl acetate, dried over anhydrous sodium sulfate and evaporated to dryness to give 9-(4-methyl-2-morpholinylmethyl)-9,10-dihydro-9,10-methanoanthracene, M.P. 136° - 137° C.

EXAMPLE 2

A mixture of 9-(3-oxo-2-morpholinylmethyl)-9,10-dihydro-9,10-methanoanthracene (100 mg) and lithium aluminum hydride (50 mg) in dioxane was stirred at 60° - 70° C for 3 hours. Excess lithium aluminum hydride was decomposed by addition of water. The reaction mixture was diluted with ethyl acetate, dried over anhydrous sodium sulfate and evaporated to dryness to give 9-(2-morpholinylmethyl)-9,10-dihydro-9,10-methanoanthracene, M.P. 183° - 189° C. Recrystallization gave colorless crystals, M.P. 189° - 190° C.

EXAMPLE 3

A mixture of 9-(4-benzyl-5-oxo-2-morpholinylmethyl)-9,10-dihydro-9,10-ethanoanthracene (1.07 g) and lithium aluminum hydride (400 mg) in dioxane was stirred at 50° -60° C for 2 hours. Excess lithium aluminum hydride was decomposed by addition of water. The reaction mixture was diluted with ethyl acetate, dried over anhydrous sodium sulfate and evaporated to dryness to give 9-(4-benzyl-2-morpholinylmethyl)-9,10-dihydro-9,10-ethanoanthracene, I.R., 3060, 3010, 2860, 2800, 1215, 1139, 1099, 1030, 980, 698, 660 cm$^{-1}$.

EXAMPLE 4

A mixture of 9-$\beta$,$\gamma$-epoxypropyl-9,10-dihydro-9,10-ethanoanthracene (0.33 g), 2-aminoethyl hydrogensulfate (1.25 g) and sodium hydroxide (0.8 g) in water was stirred in ethanol under reflux for 16 hours. The reaction mixture was concentrated and extracted with chloroform. The chloroform layer was washed with water, dried over anhydrous sodium sulfate and evaporated to dryness. The oily residue was purified over silica gel chromatography to give 9-(2-morpholinylmethyl)-9,10-dihydro-9,10-ethanoanthracene, M.P. 242° - 244° C (hydrochloride).

EXAMPLE 5

A mixture of 9-(4-acetyl-2-morpholinylmethyl)-9,10-dihydro-9,10-methanoanthracene (60 mg) and lithium aluminum hydride (30 mg) in dioxane was stirred at 60° - 70° C for 2 hours. Excess lithium aluminum hydride was decomposed by addition of water. The reaction mixture was diluted with ethyl acetate, dried over sodium sulfate and evaporated to dryness to give 9-(4-ethyl-2-morpholinylmethyl)-9,10-dihydro-9,10-methanoanthracene, M.P. 207° - 208° C (hydrochloride).

EXAMPLE 6

A mixture of 9-(2-morpholinylmethyl)-9,10-dihydro-9,10-methanoanthracene (50 mg), cyclopropylmethyl bromide (40 mg) and sodium amide (15 mg) in dry benzene was refluxed for 10 hours. The reaction mixture was diluted with benzene and water. The benzene layer was washed with water, dried over anhydrous sodium sulfate and evaporated to dryness to give 9-(4-cyclopropylmethyl-2-morpholinylmethyl)-9,10-dihydro-9,10-methanoanthracene, M.P. 88° - 90° C.

EXAMPLE 7

A mixture of 9-(2-morpholinylmethyl)-9,10-dihydro-9,10-methanoanthracene (200 mg), formic acid (600 mg) and 37% formalin (0.25 ml) was stirred at 80° C for 2 hours. 4N Hydrochloric acid was added to the cooled reaction mixture, and the reaction mixture was evaporated to dryness. The residue was diluted with water, basified with aqueous ammonia and extracted with ethyl acetate. The ethyl acetate layer was washed with water, dried over anhydrous sodium sulfate and evaporated to dryness to give 9-(4-methyl-2-morpholinylmethyl)-9,10-dihydro-9,10-methanoanthracene, M.P. 136° - 137° C.

EXAMPLE 8

A mixture of 9-(4-ethoxycarbonyl-2-morpholinylmethyl)-9,10-dihydro-9,10-methanoanthracene (400 mg) in ethanol (6 ml) and 25% aqueous sodium hydroxide solution (6 ml) was refluxed for 6 hours. The reaction mixture was diluted with water and extracted with ethyl acetate. The ethyl acetate layer was washed with water, dried over anhydrous sodium sulfate and evaporated to dryness to give 9-(2-morpholinylmethyl)-9,10-dihydro-9,10-methanoanthracene, M.P. 189° - 190° C.

EXAMPLE 9

A solution of 9-(4-benzyl-2-morpholinylmethyl)-9,10-dihydro-9,10-ethanoanthracene (150 mg) in acetic acid was added to 10% palladium on charcoal (60 mg) pretreated under hydrogen in hydrochloric acid, and the resulting mixture was stirred under hydrogen at room temperature for 14 hours. After elimination of the catalyst by filtration, the filtrate was evaporated. The residue was neutralized with 10% aqueous sodium hydroxide solution and extracted with chloroform. The chloroform extract was washed with water, dried over anhydrous sodium sulfate and evaporated to dryness. The residue was purified over silica gel chromatography to give 9-(2-morpholinylmethyl)-9,10-dihydro-9,10-ethanoanthracene, M.P. 242° - 244° C (hydrochloride).

EXAMPLE 10

A solution of 12-acetoxy-9,10-dihydro-9,10-ethanoanthracene-9-carboxylic acid (1.0 g) in benzene (10.0 ml) and thionyl chloride (4.0 ml) was refluxed for 4 hours. Evaporation of excess thionyl chloride and benzene gave 12-acetoxy-9,10-dihydro-9,10-ethanoanthracene-9-carboxylic acid chloride. The acid chloride was dissolved in dry acetone (25.0 ml), and a solution of sodium azide (0.63 g) in water (1.3 ml) was added thereto while ice cooling. The resulting mixture was stirred while ice cooling for 2 hours. The reaction mixture was diluted with water and extracted with benzene. The benzene extract was washed with water, dried over anhydrous sodium sulfate, refluxed for 2 hours and evaporated to dryness to give 9-isocyanato-12-acetoxy-9,10-dihydro-9,10-ethanoanthracene.

The isocyanate compound was dissolved in ethanol (12.0 ml) and 20% aqueous sodium hydroxide solution (12.0 ml), and the resulting solution was refluxed for 6 hours. After evaporation of ethanol, the reaction mixture was diluted with water and extracted with ethyl acetate. The ethyl acetate was washed with water, dried over anhydrous sodium sulfate and evaporated to dryness to give 9-amino-12-hydroxy-9,10-dihydro-9,10-ethanoanthracene as crystals (0.72 g), M.P. 181° - 181.5° C. Recrystallization from benzene gave analytically pure crystals of 9-amino-12-hydroxy-9,10-dihydro-9,10-ethanoanthracene, M.P. 183.5° C.

EXAMPLE 11

To a solution of 9-amino-12-hydroxy-9,10-dihydro-9,10-ethanoanthracene (3.0 g) in acetic acid (240 ml) was added a solution of sodium nitrite (6.7 g) in water (120 ml) at 2° - 5° C, and the resulting mixture was stirred at the same temperature for 1 hour and at 95° - 105° C for 5 hours. The reaction mixture was diluted with water and extracted with benzene. The benzene layer was washed with water, dried over sodium sulfate and evaporated to dryness to give crude crystals of 9-formyl-9,10-dihydro-9,10-methanoanthracene (2.8 g), which were recrystallized to give colorless crystals (2.45 g), M.P. 99° - 100° C. Further, purification by recrystallization gave analytically pure 9-formyl-9,10-dihydro-9,10-methanoanthracene, M.P. 102.5° C.

EXAMPLE 12

Triethyl phosphonoacetate (2.65 g) in benzene was treated with 50% sodium hydride dispersion in mineral oil (0.66 g), and a solution of 9-formyl-9,10-dihydro-9,10-methanoanthracene (2.0 g) in benzene (20.0 ml) was added thereto at room temperature under nitrogen. The reaction mixture was stirred at room temperature for 5 hours and at 70° C for 1 hour, diluted with water and extracted with ethyl acetate. The ethyl acetate extract was washed with water, dried over anhydrous sodium sulfate and evaporated to dryness to give β-(9,10-dihydro-9,10-methano-9-anthryl)acrylic acid ethyl ester. A solution of the ethyl ester in methanol (53 ml) and 10% aqueous sodium hydroxide (12 ml) was refluxed for 4 hours. The reaction mixture was diluted with water, acidified with hydrochloric acid and extracted with ethyl acetate. The ethyl acetate extract was washed with water, dried over anhydrous sodium sulfate and evaporated to dryness to give β-(9,10-dihydro-9,10-methano-9-anthryl)-acrylic acid, M.P. 219.5° − 222° C.

EXAMPLE 13

A mixture of β-(9,10-dihydro-9,10-methano-9-anthryl)acrylic acid (612 mg) and 5% palladium-charcoal (120 mg) in ethanol was stirred under hydrogen atmosphere at room temperature for 2 hours. The catalyst was removed by filtration, and the solution was evaporated to dryness to give β-(9,10-dihydro-9,10-methano-9-anthryl)propionic acid, M.P. 185° − 189° C.

EXAMPLE 14

A mixture of β-(9,10-dihydro-9,10-methano-9-anthryl)propionic acid dimethyl amide(6.0 g) and lithium aluminum hydride in dioxane was stirred at 50° − 60° C for 2 hours. Excess lithium aluminum hydride was decomposed by addition of water. The reaction mixture was diluted with ethyl acetate, dried over anhydrous sodium sulfate and evaporated to dryness to give 9-γ-dimethylaminopropyl-9,10-dihydro-9,10-methanoanthracene, M.P. 247° − 247.5° C (hydrochloride).

The starting amide was prepared as follows:

A solution of β-(9,10-dihydro-9,10-methano-9-anthryl)propionic acid and thionyl chloride in benzene was refluxed for 4 hours. Evaporation of excess thionyl chloride and benzene gave β-(9,10-dihydro-9,10-methanoanthryl)propionic acid chloride, which was dissolved in dry tetrahydrofuran. The solution was added to a 30% aqueous dimethylamine solution at 0° − 5° C. The reaction mixture was stirred at 0°− 15° C, diluted with water and extracted with ethyl acetate. The ethyl acetate layer was washed with water, dried over anhydrous sodium sulfate and evaporated to dryness to give β-(9,10-dihydro-9,10-methano-9-anthryl)-propionic acid dimethylamide, M.P. 186° − 187° C.

EXAMPLE 15

9-γ-Dimethylaminopropyl-9,10-dihydro-9,10-methanoanthracene (1.0 g) was converted to 9-γ-trimethyl-ammoniumpropyl-9,10-dihydro-9,10-methanoanthracene iodide by treatment with methyl iodide in ethyl acetate. The ammonium iodide was treated with silver oxide in methanol and water for 3 hours. The resulting precipitate was removed by filtration. The filtrate was evaporated to dryness on a water bath (90° − 95° C) under reduced pressure and the residue was heated at 95° C for 7 hours under reduced pressure. Benzene was added to the reaction mixture, and the benzene layer was washed with water, dried over anhydrous sodium sulfate and evaporated to dryness to give crude crystals, which was purified over silica gel chromatography to give colorless crystals of 9-β-propenyl-9,10-dihydro-9,10-methanoanthracene, M.P. 63° − 64° C.

By a similar manner, 9-γ-dimethylaminopropyl-9,10-dihydro-9,10-ethanoanthracene was converted to 9-β-propenyl-9,10-dihydro-9,10-ethanoanthracene, M.P. 42° − 43° C.

EXAMPLE 16

A mixture of 9-β-propenyl-9,10-dihydro-9,10-ethanoanthracene-11-one (280 mg), hydrazine (0.2 ml) and sodium hydroxide in triethyleneglycol was stirred at 150° C for 30 minutes and at 190° − 200° C for 2.5 hours. The reaction mixture was diluted with water and extracted with benzene. The organic layer was washed with water, dried over anhydrous sodium sulfate and evaporated to dryness. The residue was purified over silica gel chromatography to give 9-β-propenyl-9,10-dihydro-9,10-ethanoanthracene, M.P. 42° − 43° C.

EXAMPLE 17

A solution of 9-β-propenyl-9,10-dihydro-9,10-ethanoanthracene (1.1 g) and m-chloroperbenzoic acid (1.6 g) in ether was stirred at room temperature for 5 days. The solution was diluted with benzene, washed with aqueous sodium hydroxide solution and water, dried over anhydrous sodium sulfate and evaporated to dryness to give 9-β,γ-epoxypropyl-9,10-dihydro-9,10-ethanoanthracene as an oil, I.R., 3070, 3040, 3020, 2860, 1263, 1140, 1033, 830, 760, 680, 630 cm$^{-1}$.

EXAMPLE 18

A mixture of 9-β,γ-epoxypropyl-9,10-dihydro-9,10-ethanoanthracene (1.07 g) and benzylamine (1.31 g) was stirred at 80° C for 9 hours. The reaction mixture was diluted with ethyl acetate, washed with water, dried over anhydrous sodium sulfate and evaporated to dryness. The oily residue was purified over silica gel chromatography to give 9-β-hydroxy-γ-benzylaminopropyl-9,10-dihydro-9,10-ethanoanthracene as an oil, I.R., 3350, 3060, 3015, 2860, 1600, 1138, 1105, 1030, 980, 695, 660 cm$^{-1}$.

EXAMPLE 19

9-β-Hydroxy-γ-benzylaminopropyl-9,10-dihydro-9,10-ethanoanthracene (1.01 g) was dissolved in dichloromethane. After addition of 50% aqueous sodium hydroxide solution (0.24 g), chloroacetyl chloride (0.34 g) was added to the solution at 0° − 5° C. The reaction mixture was stirred at room temperature for 4.5 hours. The organic layer was washed with water, dried over anhydrous sodium sulfate and evaporated to dryness to give an oily residue. A mixture of the residue and 65.4% sodium (oily dispersion, 1.0 g) in benzene was stirred at room temperature for 1.5 hours and refluxed for 40 hours. The reaction mixture was washed with water, dried over anhydrous sodium sulfate and evaporated to dryness. The residue was purified over silica gel chromatography to give 9-(4-benzyl-5-oxo-2-morpholinylmethyl)-9,10-dihydro-9,10-ethanoanthracene, I.R. (Nujol), 1656, 1263, 1125, 1088, 1030, 980, 757, 720, 695, 665 cm$^{-1}$.

EXAMPLE 20

A mixture of α-bromo-β(9,10-dihydro-9,10-methano-9-anthryl)propionic acid N-benzyl-N-hydroxyethylamide (1.25 g) and 65.4% sodium hydride (oily dispersion, 0.19 g) in dry benzene was stirred at room temperature for 7 hours. The reaction mixture was washed with water, dried over anhydrous sodium sulfate and evaporated to dryness to give 9-(4-benzyl-3-oxo-2-morpholinylmethyl)-9,10-dihydro-9,10-methanoanthracene, M.P. 155° - 156° C.

In a similar manner, α-bromo-β-(9,10-dihydro-9,10-ethano-9-anthryl)propionic acid N-benzyl-N-hydroxyethylamide was led to 9-(4-benzyl-3-oxo-2-morpholinylmethyl)-9,10-dihydro-9,10-ethanoanthracene, I.R., 3060, 3008, 2860, 1640, 1240, 1212, 1123, 1026, 962, 922, 698 cm⁻¹.

The starting material, α-bromo-β-(9,10-dihydro-9,10-methano-9-anthryl)propionic acid N-benzyl-N-hydroxyethylamide, was prepared as follows:

9-Formyl-9,10-dihydro-9,10-methanonanthracene was condensed with diethyl malonate or cyanoethyl acetate in the presence of a base. The condensed product was reduced by catalytic hydrogenation or treatment with sodium borohydride, followed by hydrolysis to give α-carboxy-β-(9,10-dihydro-9,10-methano-9-anthryl)propionic acid.

α-Carboxy-β-(9,10-dihydro-9,10-methano-9-anthryl)propionic acid was treated with bromine in ether, and the corresponding brominated compound was refluxed in xylene to give α-bromo-β-(9,10-dihydro-9,10-methano-9-anthryl)propionic acid. α-Bromo-β-(9,10-dihydro-9,10-methano-9-anthryl)-propionic acid was treated with thionyl chloride and then with N-benzyl-N-hydroxyethylamine to give α-bromo-β-(9,10-dihydro-9,10-methano-9anthryl)propionic acid N-benzyl-N-hydroxyethylamide, I.R., 3400, 3060, 3045, 2860, 1640, 1360, 1158, 1048, 1012, 698 cm⁻¹.

EXAMPLE 21

A solution of 9-(4-benzyl-2-morpholinylmethyl)-9,10-dihydro-9,10-methanoanthracene (590 mg) and chloroethyl carbonate (671 mg) in dry toluene was refluxed for 3 hours. The reaction solution was washed with water, dried over anhydrous sodium sulfate and evaporated to dryness to give 9-(4-ethoxycarbonyl-2-morpholinylmethyl)-9,10-dihydro-9,10-methanoanthracene, M.P. 143° - 144.5° C.

The following compounds were produced by one or more of the procedures as described above:

9-(2-Morpholinylmethyl)-9,10-dihydro-9,10-methanoanthracene, M.P. 189° - 190° C;

9-(4-Methyl-2-morpholinylmethyl)-9,10-dihydro-9,10-methanoanthracene, M.P. 136° - 137° C;

9-(4-Ethyl-2-morpholinylmethyl)-9,10-dihydro-9,10-methanoanthracene hydrochloride, M.P. 207° - 208° C;

9-(4-Isopropyl-2-morpholinylmethyl)-9,10-dihydro-9,10-methanoanthracene, M.P. 163.5° - 166° C;

9-(4-Benzyl-2-morpholinylmethyl)-9,10-dihydro-9,10-methanoanthracene, M.P. 140° - 142° C;

9-(4-Allyl-2-morpholinylmethyl)-9,10-dihydro-9,10-methanoanthracene hydrochloride, M.P. 214° - 217° C;

9-(4-Cyclopropylmethyl-2-morpholinylmethyl)-9,10-dihydro-9,10-methanoanthracene, M.P. 88° - 90° C;

9-(2-Morpholinylmethyl)-9,10-dihydro-9,10-ethanoanthracene hydrochloride, M.P. 242° - 244° C;

9-(4-Methyl-2-morpholinylmethyl)-9,10-dihydro-9,10-ethanoanthracene hydrochloride, M.P. 273° - 276° C;

9-(4-Isopropyl-2-morpholinylmethyl)-9,10-dihydro-9,10-ethanoanthracene hydrochloride, M.P. 257° - 258.5° C;

9-(4-Benzyl-2-morpholinylmethyl)-9,10-dihydro-9,10-ethanoanthracene, I.R. (neat), 3060, 3010, 2860, 2800, 1215, 1139, 1099, 1030, 980, 698, 660 cm⁻¹;

9-(4-Allyl-2-morpholinylmethyl)-9,10-dihydro-9,10-ethanoanthracene hydrochloride, M.P. 219° - 220° C;

9-(4-Cyclopropylmethyl-2-morpholinylmethyl)-9,10-dihydro-9,10-ethanoanthracene hydrochloride, M.P. 264° - 267° C.

What is claimed is:

1. A compound of formula:

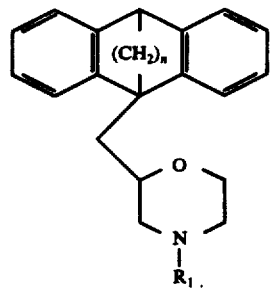

wherein $R_1$ is hydrogen, $C_1$–$C_4$ alkyl, $C_3$–$C_5$ alkenyl, phenyl($C_1$–$C_4$)alkyl or ($C_3$–$C_6$)cycloalkyl($C_1$–$C_4$)alkyl and $n$ is 1 or 2, or a non-toxic salt thereof.

2. The compound according to claim 1, wherein $n$ is 1, or a non-toxic salt thereof.

3. The compound according to claim 2, wherein $R_1$ is hydrogen, methyl or benzyl and $n$ is 1, or a non-toxic salt thereof.

4. 9-(2-Morpholinylmethyl)-9,10-dihydro-9,10-methanoanthracene, or a non-toxic salt thereof.

5. 9-(4-Benzyl-2-morpholinylmethyl)-9,10-dihydro-9,10-methanoanthracene, or a non-toxic salt thereof.

6. An antidepressant composition which comprises a therapeutically effective amount of at least one compound according to claim 1 as an active ingredient and a pharmaceutically acceptable carrier or diluent.

7. A method for treatment of mental depression which comprises administering to a human an effective amount of at least one compound according to claim 1.

* * * * *